United States Patent [19]
Raymond

[11] Patent Number: 5,639,460
[45] Date of Patent: Jun. 17, 1997

[54] AQUEOUS PLANT EXTRACT HAVING ANTIVIRAL ACTIVITY

[76] Inventor: Hal C. Raymond, 572 Valley View Dr., Hyrum, Utah 84319

[21] Appl. No.: 479,602

[22] Filed: Jun. 7, 1995

[51] Int. Cl.$^6$ ................................................ A61K 35/78
[52] U.S. Cl. ........................................ 424/195.1; 514/934
[58] Field of Search ........................ 424/195.1; 514/934

[56] References Cited

U.S. PATENT DOCUMENTS

| | | | |
|---|---|---|---|
| Re. 31,836 | 2/1985 | Horrobin | 514/474 |
| 4,285,934 | 8/1981 | Tinnell | 424/195.1 |
| 4,887,924 | 12/1989 | Green | 401/261 |
| 4,888,326 | 12/1989 | Horrobin | 514/27 |
| 4,996,233 | 2/1991 | Horrobin | 514/560 |
| 5,145,686 | 9/1992 | Horrobin et al. | 424/677 |
| 5,216,142 | 6/1993 | Horrobin et al. | 514/50 |
| 5,252,333 | 10/1993 | Horrobin | 424/42.2 |
| 5,276,020 | 1/1994 | Horrobin et al. | 514/45 |
| 5,328,691 | 7/1994 | Horrobin et al. | 424/401 |
| 5,405,835 | 4/1995 | Mendy | 514/21 |

OTHER PUBLICATIONS

George Pettit, et al., Chem. Abst. 79:123648, "Antineoplastic agents.31. Oenothera caespitosa". 1973.
Zinsmeister et al., "Flavonol Glycosides in South American Species Of Oenothera Sect. Oenothera", Phytochemistry, 1977, vol. 16, p. 497.
G. Neumann et al., "Organ-and-Tissue-specific Biosynthesis of Flavonoids in Seedlings of Oenothera odorate (Onagraceae)", Bot. Acta 107, pp. 95-102, 1994.
Petit et al., "Antineoplastic Agents 31. Oenothera caespitosa" *Lloydia*, pp. 202-203 (1973).

*Primary Examiner*—John W. Rollins
*Attorney, Agent, or Firm*—Trask, Britt & Rossa

[57] ABSTRACT

An aqueous extract of *Oenothera caespitosa* having antiviral activity. Compositions containing such an extract are especially effective in topically treating herpes simplex lesions. Methods of making and using the extract are also disclosed. Topically applied compositions relieve pain and promote healing of lesions caused by the herpes simplex virus, varicella virus, and Epstein-Barr virus. The composition may also reduce the recurrence of herpes simplex lesions and act as a prophylactic agent by interrupting the spread of the virus and subsequent vesicle and lesion formation.

15 Claims, 1 Drawing Sheet

AQUEOUS PLANT EXTRACT HAVING ANTIVIRAL ACTIVITY

TECHNICAL FIELD

The invention generally relates to a composition and method for treating viral infections and, more particularly, to an extract of evening primrose having antiviral activity against viral infections including herpes simplex virus.

STATE OF THE ART

Herpes simplex virus is one of the most prevalent recurrent and chronic infections seen in the medical profession. An estimated 75 percent of the United States population has been infected with the herpes simplex virus. While the majority of cases are asymptomatic, chronic outbreaks of lesions are very common, usually occurring in mucous membrane areas and the surrounding skin. The most common of these lesions occur as orofacial lesions commonly referred to as "cold sores" or "fever blisters."

The lesions initially appear as an area of irritation and edema, which develop into small vesicles within a few hours. Generally, the vesicles rapidly rupture to form shallow ulcerations which scab and heal in about two to three weeks. The rupturing vesicles also release exudate which causes secondary infections and spreads the virus to surrounding skin or mucous membranes.

Following the initial exposure to the herpes simplex virus, the host develops antibodies which can maintain the virus in a latent state. Despite the presence of antibodies, the latent virus may be reactivated by a number of factors such as stress, ultraviolet ray exposure, fever, hormonal changes, menstruation, and tissue trauma. As a result of the many activating factors, local eruptions recur randomly and take the usual two to three week period to heal.

Currently, a systemic cure for herpes simplex is not known. Furthermore, once a vesicle is formed, systemic anti-infectives would probably be ineffective because of the low or non-existent blood flow to the infected fluid area within the vesicle. In contrast, topical therapy facilitates absorption of active ingredients into the affected area and would be expected to interrupt viral replication in the vesicles and lesions, thus expediting the healing process of the resulting lesion. Because topical routes of administration only act locally, latent viruses would not be affected.

In the patent literature, the use of some Evening Primrose species (e.g. *Oenothera biennis L.* and *Oenothera lamarckiana*) is described as treatments for various physical disorders. For example, Horrobin, reissued U.S. Pat. No. Re. 31,836, discloses the use of *Oenothera biennis L.* and *Oenothera lamarckiana*, as a source of gamma-linoleic acid oil, in conjunction with ascothic acid, ethyl alcohol, and opiate antagonists for treating alcoholism.

The use of Evening Primrose as a carrier in antiviral compositions is also disclosed in the literature. Horrobin et al., U.S. Pat. No. 5,216,142, and Horrobin et al., U.S. Pat. No. 5,276,020, describe the use of *Oenothera biennis* as a source of fatty acids. The fatty acids are utilized to enhance the transport of the composition's active antiviral agents across lipid barriers in the body. Horrobin, U.S. Pat. No. 5,252,333, discloses pharmaceutical and disinfectant compositions containing lithium salts of polyunsaturated fatty acids. The fatty acids, which are derived from Evening Primrose oil, are included as carriers for the lithium salts and impart lipid solubility to the composition.

The use of topical compositions for treatment of herpes virus infections is disclosed in the literature. Tinnell, U.S. Pat. No. 4,285,934, discloses a suspension of boric acid, tannic acid, and salicylic acid in a special solvent for the topical treatment of herpes genitalis and herpes simplex viruses.

The literature is not believed to describe a manner and process of making and using an aqueous extract of Evening Primrose to treat herpes simplex lesions. More specifically, the literature is not believed to describe an aqueous extract of *Oenothera caespitosa* to treat any physical disorders.

DISCLOSURE OF THE INVENTION

An aqueous extract of *Oenothera caespitosa* has been found to be an effective topical treatment of herpes simplex lesions. The invention thus includes a composition containing a water-soluble extract prepared from plants of the species *Oenothera caespitosa*. The composition is useful for, among other things, treating lesions caused by the herpes simplex virus.

The invention also includes a method of treating herpes simplex virus lesions in mammals. The method involves topically applying a composition comprising a water-soluble extract prepared from plants of the species *Oenothera caespitosa* to the lesions caused by the herpes simplex virus.

The topically applied composition relieves and promotes the healing of lesions caused by the herpes simplex virus. The composition may also reduce the recurrence of herpes simplex lesions and act as a prophylactic agent by interrupting the spread of the virus and subsequent vesicle and lesion formation.

The invention also includes a process for making a composition for treating viral infections such as herpes simplex virus lesions. The invention thus includes the use of an aqueous extract of the genus Oenothera for use in a method for the treatment of a mammalian body, which body is suffering from a viral infection, such as herpes simplex virus lesions.

BEST MODE OF THE INVENTION

Figure 1:
FIG. 1 graphically depicts a plant characterized as *Oenothera caespitosa* herein.

The *Oenothera caespitosa* species of the Evening Primrose plant contains the active ingredients for use in the topical treatment of herpes simplex lesions. The active ingredients are extracted from mature plants and plant parts (e.g. leaves, stems, flowers, buds, etc.). Preferably, the flower, bud, or both flower and bud portions of a mature plant are used in the extraction process.

The various plant parts may come from freshly cut plants or may be extracted from dried plant parts. Methods for extraction, and various extractives, definitionally, are described in J. G. Nairn, *Remington's Pharmaceutical Sciences*, Mack Printing Co., Easton, Pa. (17th ed. 1985) at pages 1516–1517, the contents of which are incorporated by this reference.

Based on the water-soluble properties of the active ingredients extracted from the plant parts, the extraction procedure will preferably utilize a hydrophilic/polar (water soluble) solvent (e.g. water, alcohol, glycerol, and hydroalcoholic solvents). The use of a hydrophilic solvent also facilitates evaporation of all or nearly all of the solvent, leaving a residual mass or powder of the concentrated composition.

A preferred method of small scale extraction involves placing an amount (e.g. from about 400 milligrams ("mg")

to about 2000 mg) of the flower, bud, or both flower and bud from a mature *Oenothera caespitosa* plant into a container of water (e.g. one containing from about 120 milliliters ("ml") to about 180 ml) which has been heated to a boil. The heat is then removed and the plant part(s) left to steep, as in the preparation of a tea, until much of the coloration of the flower is removed from the plant part(s) and the boiled water has cooled to room temperature. Through this process, the active ingredients are extracted from the plant parts into the water in the form of a water soluble composition.

The vehicles of the composition, when used, are preferably non-toxic in the amounts used and must be able to act as a vehicle for the aqueous extract (i.e. have the proper polarity). A fluid vehicle is preferably also used in the extraction process to save processing steps. However, an alcohol (e.g. isopropyl alcohol) or other solvent extraction of the active ingredients from the plant parts and subsequent admixture of the extract with a chosen fluid vehicle will also suffice. This is particularly important where the active ingredients form part of a water-in-oil emulsion (e.g. creams and lotions) which can facilitate the controlled release and administration of the composition to the affected areas.

Preferably, both the solvent and vehicle may be any substance which does not react with the composition to reduce its efficacy. Alcohol, water, or a hydroalcoholic mixture are all appropriate for use as solvents and vehicles. Where quick evaporation is preferred, alcohol is the preferred solvent and vehicle. The preferred alcohols are ethanol and isopropyl alcohol.

Treatment may be effected by applying a small quantity of the composition directly to the portion of the body (e.g. mouth area, genitalia, lower back, face, etc.) believed to be infected with virus (e.g. lesions). Depending on the vehicle used, the composition may be applied with a sponge, cotton swab, applicator tube, or any other appropriate and convenient administration method. A sufficient quantity of the composition should be used to fully cover the lesions and should be preferably applied twice daily for approximately three days. In most cases, pain, swelling, and irritation cease within a few hours after the initial application. Healing of the lesion occurs within one to three days after the initial application. Upon application of the composition at the immediate onset of the herpes eruption or irritation of the tissue, vesicle formation, spreading, and secondary infections to surrounding areas are prevented. Lesions usually clear within two to three days with little or no scarring.

An effective amount of the composition is an amount sufficient to inhibit the progress of the particular viral infection in the affected mammal. Inhibition of the progress can be measured by, for example, viewing the growth or decline of the lesions, measuring the amount of time between reoccurrences, and measuring the amount of infected skin area.

The composition also appears to have a retardant effect on the virus, prolonging the time period between reappearance of the lesions. In at least one case, the herpes simplex eruptions are believed to have been eliminated altogether. In all cases, high rates of remission of the herpes simplex lesions on orofacial mucosa and surrounding skin tissue have been obtained following treatment in accordance with the invention.

The composition has also displayed activity against varicella zoster virus ("VZV" the causative agent for chicken pox and shingles) and Epstein-Barr virus. It has also been useful in treating warts and mononucleosis.

The following illustrative EXAMPLES also help to explain the invention:

EXAMPLES

EXAMPLE I

Samples of extract from the flower of the *Oenothera caespitosa* plant were submitted to the National Institute of Allergy and Infectious Diseases, Bethesda, Md., for testing of anti-herpetic activity. The testing included a cytopathic effect inhibition assay and a plaque reduction assay for both herpes simplex virus serotypes 1 (HSV-1) and 2 (HSV-2).

The cytopathic effect inhibition assay consisted of seeding low passage human foreskin fibroblast cells into 96 well tissue culture plates 24 hours prior to use. A cell concentration of $2.5 \times 10^4$ cells per ml in 0.1 ml of minimal essential medium ("MEM") supplemented with 10% fetal bovine serum ("FBS") was used for the culture plates. The cells were then incubated for 24 hours at 37° C. in a $CO_2$ incubator. After incubation, the medium was removed and 100 mcl of MEM containing 2% FBS was added to all but the first row. In the first row, 125 mcl of the extract was added in triplicate wells. Medium alone was added to both cell and virus control wells. The extract applied to the first row of wells was then diluted serially 1:5 throughout the remaining wells by transferring 25 mcl of MEM using the Cetus Liquid Handling Machine. After dilution of the extract, 100 mcl of HSV-1 and HSV-2, at a concentration of 1000 plaque forming units, per well was added, excluding cell control wells which received 100 mcl of MEM. The plates were then incubated at 37° C. in a $CO_2$ incubator for three days. After the incubation period, media was aspirated and the cells stained with a 0.1% crystal violet solution for 30 minutes. The stain was then removed and the plates rinsed using tap water until all excess stain was removed. The plates were allowed to dry for 24 hours and then read on a Skatron Plate Reader at 620 nm. The extract samples demonstrated antiviral selectivity against both HSV-1 and HSV-2. The concentration required to inhibit viral cytopathogenicity by 50% ($EC_{50}$) was 11 mcg/ml for the HSV-1 and 3.8 mcg/ml for the HSV-2.

The plaque reduction assay consisted of plating HSV-1 and HSV-2 into six well plates and incubating the plates at 37° C. with 5% $CO_2$ at 90% humidity. The plates were incubated for two days. On the date of the assay, the extract was made up at six varying concentrations, using 2X MEM and then serially diluting the extract with the same. The concentration of extract used varied from 200 micrograms/ml down to 0.06 micrograms/ml. HSV-1 and HSV-2 were diluted in MEM containing 10% FBS to a desired concentration providing 20–30 plaques per well. The media was then aspirated from the wells and 0.2 ml of HSV-1 or HSV-2 was added to each well. The plates were then incubated for one hour and shaken every fifteen minutes. After the incubation period, an equal amount of 1% agarose was added to an equal volume of each extract dilution. This produced final drug concentrations from 100 micrograms/ml to 0.03 micrograms/ml and a final agarose overlay concentration of 0.5%. Two milliliters of the extract-agarose mixture was applied to each well and the plates were then incubated for three days. The cells were then stained with a 1.5% solution of neutral red. After a subsequent 4–6 hour incubation period, the stain was aspirated and plaques were counted using a stereo-microscope at 10× magnification. The extract samples demonstrated antiviral selectivity against both HSV-1 and HSV-2. The $EC_{50}$ was 24 mcg/ml and 40 mcg/ml for the HSV-1 and 40 mcg/ml for the HSV-2.

EXAMPLE II

A person had multiple herpes simplex lesions spread over the lower and upper lip areas and surrounding skin.

Historically, formation of the lesions would occur approximately every two months and usually lasted from one to two weeks, starting with one lesion and rapidly spreading over the realm of the lip area within a few days. Various over-the-counter cold sore medications were tried over the years without success. An aqueous extraction of *Oenothera caespitosa* was prepared by boiling 180 ml water, removing the boiling water from the heat source, introducing a single flower from a *Oenothera caespitosa* plant, and allowing the water to cool to room temperature. The resulting extract found in the water was soaked into a sponge. The extract was then applied onto the lesions and vesicles with the sponge for approximately five minutes. Within twelve hours after treatment, the vesicles disappeared and all the lesions appeared to diminish in size and number. For over two years after the initial treatment of the lesions, no recurrence of herpes simplex eruptions has been reported.

EXAMPLE III

Another subject had multiple herpes simplex lesions on the lower and upper lip areas. The lesions had been recurring about every three (3) months for the last twenty (20) years. The individual tried various over-the-counter cold sore medications without success. A single flower from an *Oenothera caespitosa* plant was added to a bowl of boiled water and allowed to soak for a few minutes. The saturated flower was then directly applied to the herpes simplex lesions for approximately thirty seconds. This process was repeated for two to three minutes. The treatment was then repeated approximately six hours after the initial treatment. The pain accompanying the lesions disappeared shortly after the second treatment and the spread of the vesicles and lesions was prevented. Additionally, the lesions and vesicles continued to decrease in size and had substantially disappeared within a twenty-four hour period after the initial treatment.

Within a few months, the individual noticed a slight pain and small bump on the lip area which indicated a recurrence of the herpes simplex virus. The same process outlined above was used on the irritated lip area. Within twenty-four hours, the pain and small bump had completely disappeared.

EXAMPLE IV

A femme had two herpes simplex lesions about the lip area. The lesions had been recurring about two to three times per year for the last twenty-three (23) years. The normal course of the infection included about seven days of extreme soreness and resulting secondary infections. Complete healing usually takes a minimum of seven days. The individual tried various over-the-counter cold sore medications without success and a prescription antiviral that achieved limited success. The treatment method of the previous EXAMPLE was used and applied to the lesions for variable periods of time and consistently throughout the work day. The growth in size and number of vesicles and lesions was halted. The pain and irritation accompanying the lesions was also eradicated within twenty-four hours. The treatment was continued for a total of three days, resulting in the scabbing and subsequent disappearance of the two lesions within thirty-six hours after the initial treatment.

EXAMPLE V

An ointment was made containing:

| | |
|---|---|
| water extract of EXAMPLE II | 20 teaspoons |
| VASELINE ™ petroleum jelly | 16 ozs. |
| Eucalyptus oil | 20 drops |
| Camphor | 20 drops |
| Tea tree oil | 10 drops |

The ointment was mixed, and subsequently applied to skin lesions on two subjects suffering from herpes simplex virus.

Although the invention has been described in detail with respect to a specific extract, methods of extraction, and methods of treatment, it should be realized that certain modifications can be made within the scope and spirit of the invention by those skilled in the art. For example, the addition of other antiviral ingredients, preservatives, and changes in the solvent or carrier are contemplated. Therefore, the invention should be limited only by the following claims.

What is claimed is:

1. A process of manufacturing a composition for treating herpes simplex virus lesions in mammals, said process comprising:

heating from 120 parts by weight water to about 180 parts by weight water to a boil;

placing from about 0.4 parts to about 2 parts by weight material from a mature Oenothera plant into the water;

cooling said water to room temperature further extracting the water soluble ingredients from the material; and removing the material from the water.

2. The process according to claim 1, wherein said material is a flower from a mature *Oenothera caespitosa* plant.

3. The process according to claim 1, wherein said material is a bud from a mature *Oenothem caespitosa* plant.

4. The process according to claim 1, wherein said material is in a dry form.

5. The process according to claim 1, wherein an extract is removed from the remainder of the admixture by siphoning the top of the admixture.

6. The process according to claim 1, wherein an extract is removed from the remainder of the admixture by decanting the admixture, leaving the extract behind in the lower liquid layers.

7. The process according to claim 1, wherein an extract is removed from the remainder of the admixture by filtering the admixture and removing the extract as a filtrate.

8. A composition produced by the process of claim 1.

9. A method for treating a mammal suffering from herpes simplex virus lesions comprising topically applying to the herpes simplex virus lesions a composition comprising a water-soluble extract prepared from plants of the species *Oenothera caespitosa*.

10. The method of claim 9, wherein said composition is applied to the lesions prophylactically to prevent further herpes simplex virus eruptions.

11. The method of claim 9 further comprising reapplying said composition in a sufficient amount to continue the treatment of the virus lesions and prevent reinfection.

12. A method for treating a portion of a mammalian body believed to be suffering from a virus selected from the group of viruses consisting of herpes simplex virus, varicella virus, Epstein-Barr virus, and the causative agent for warts, comprising topically applying a composition comprising a water-soluble extract of *Oenothera caespitosa* to the body portion believed to be infected with said virus.

13. The method of claim 8 wherein the composition applied to the body portion believed to be infected with said virus further comprises a solvent capable of taking into solution said water-soluble extract.

14. A method for preventing the occurrence of herpes simplex viral lesions in a mammal who has previously had herpes simplex viral lesions on an area of the mammal's body, said method comprising topically applying to said area of the mammal's body a composition comprising a water-soluble extract prepared from plants of the species *Oenothera caespitosa*.

15. The method of claim 14 wherein the solvent in the composition applied to the body portion believed to be infected with said virus is selected from the group of solvents consisting of water, ethyl alcohol, isopropyl alcohol, glycerin, propylene glycol, and combinations thereof.

* * * * *

UNITED STATES PATENT AND TRADEMARK OFFICE
CERTIFICATE OF CORRECTION

PATENT NO. : 5,639,460
DATED : June 17, 1997
INVENTOR(S) : Hal C. Raymond

It is certified that error appears in the above-indentified patent and that said Letters Patent is hereby corrected as shown below:

In column 1, line 52, delete "ascothic" and insert --ascorbic-- therefor;

In column 2, line 55, delete "Pa." and insert --PA-- therefor;

In column 3, line 63, insert a comma after VZV;

In column 4, line 5, delete "Md" and insert --MD-- therefor;

In column 5, line 50, delete "femme" and insert --female-- therefor; and

In column 6, line 38, delete "oenothem" and insert --Oenothera-- therefor.

Signed and Sealed this

Twenty-eighth Day of October, 1997

Attest:

BRUCE LEHMAN

Attesting Officer

Commissioner of Patents and Trademarks